United States Patent [19]

Hart et al.

[11] Patent Number: 5,211,559
[45] Date of Patent: May 18, 1993

[54] DENTAL TREATMENT TRAY FOR HOLDING MEDICAMENT GEL

[75] Inventors: Adrian Hart, Menlo Park; John A. Kaminski, Newark, both of Calif.

[73] Assignee: Gillette Canada Inc., Kirkland, Canada

[21] Appl. No.: 893,185

[22] Filed: Jun. 2, 1992

Related U.S. Application Data

[63] Continuation-in-part of Ser. No. 732,480, Jul. 18, 1991, abandoned.

[51] Int. Cl.$^5$ .................. A61G 17/02; A61C 9/00; A61K 7/18
[52] U.S. Cl. ................................. 433/80; 433/37; 433/42; 433/43; 424/52
[58] Field of Search .................. 433/37, 42, 43, 80, 433/89; 128/861

[56] References Cited

U.S. PATENT DOCUMENTS

| | | | |
|---|---|---|---|
| Re. 28,667 | 12/1987 | Gores | 128/136 |
| Re. 31,787 | 1/1985 | Chang | 424/52 |
| D. 228,048 | 8/1983 | Miller . | |
| D. 263,073 | 2/1982 | Jonkers et al. | D24/10 |
| D. 273,893 | 5/1984 | Weitzman | 433/42 |
| D. 278,274 | 4/1985 | Levine . | |
| D. 281,529 | 11/1985 | Seid et al. . | |
| D. 281,530 | 11/1985 | Seid et al. . | |
| 730,658 | 6/1903 | Huber . | |
| 767,553 | 8/1904 | Edgelow . | |
| 803,474 | 10/1905 | Dennis . | |
| 803,475 | 10/1905 | Dennis . | |
| 905,535 | 12/1908 | Holmes | 433/43 |
| 1,910,740 | 5/1933 | Barsha . | |
| 2,001,963 | 5/1935 | Keller . | |
| 2,171,695 | 9/1939 | Harper . | |
| 2,257,709 | 9/1941 | Anderson . | |
| 2,590,118 | 3/1952 | Oddo, Jr. . | |
| 2,696,668 | 5/1953 | Fox . | |
| 2,703,452 | 3/1955 | Getz . | |
| 2,847,003 | 8/1958 | Helmer et al. . | |
| 2,857,909 | 10/1958 | Johnson . | |
| 2,966,908 | 1/1961 | Cathcart et al. . | |
| 3,060,935 | 10/1962 | Riddell . | |
| 3,148,103 | 9/1964 | Gallagher . | |
| 3,234,942 | 1/1966 | Simor . | |
| 3,312,218 | 4/1967 | Jacobs . | |

(List continue on next page.)

OTHER PUBLICATIONS

Dental Services; Austin H. Kutscher, DDS, School of Dental and Oral Surgery Columbia Unversity, NY; Date unknown pp. 1886–1896 Chapter 105. Dental Services.

*Primary Examiner*—Gene Mancene
*Assistant Examiner*—Cindy A. Cherichetti
*Attorney, Agent, or Firm*—Oblon, Spivak, McClelland, Maier & Neustadt

[57] ABSTRACT

A gel tray for holding a medicament to be applied to the teeth and gums of a patient includes a handle and an opposing buckle. In one embodiment, the buckle includes a tongue portion and a retainer strip surrounding the tongue portion so as to define a narrow space between the tongue portion and the retainer strip, the narrow strip having a width less than the thickness of the handle. The handle has a tongue reception groove extending transverse to its length at a position such that the tongue reception groove is engaged by the tongue when the tray is folded. In another embodiment, slotted tabs are interfitted when the tray is folded. The tray may therefore be securely maintained in the folded state. The tray can be combined with or preloaded with a treatment agent such as a gel comprising a pharmaceutically effective amount of at least one agent for treating teeth or gums dispersed in a gel medium consisting essentially of water and an amount of a water dispersible gelling agent sufficient to form a gel. Preferably, the treatment gel comprises an agent such as from 0.05 to 5 wt. % of a soluble fluoride, either in an acidic gel or a neutral. Acidic gels can contain pharmaceutically acceptable, treatment effective amounts of phosphoric acid and hydrofluoric acid, for example. Neutral gels can have pH modifying agents such as sodium hydroxide.

31 Claims, 4 Drawing Sheets

U.S. PATENT DOCUMENTS

| | | | |
|---|---|---|---|
| 3,339,547 | 9/1967 | Drabkowski . | |
| 3,407,809 | 10/1968 | Ross . | |
| 3,429,963 | 2/1969 | Shedlovsky . | |
| 3,448,738 | 6/1969 | Berghash . | |
| 3,468,029 | 9/1969 | Moore . | |
| 3,527,219 | 9/1970 | Greenberg . | |
| 3,536,069 | 10/1970 | Gores . | |
| 3,577,700 | 5/1971 | Bippes . | |
| 3,589,592 | 6/1971 | Tigner . | |
| 3,624,909 | 12/1971 | Greenberg . | |
| 3,657,044 | 4/1972 | Singer . | |
| 3,682,164 | 8/1972 | Miller . | |
| 3,874,084 | 4/1975 | Cole . | |
| 3,954,537 | 5/1976 | Alfter et al. | 156/82 |
| 3,955,281 | 5/1976 | Weitzman . | |
| 3,956,480 | 5/1976 | Dichter et al. | 424/54 |
| 4,003,132 | 1/1977 | Beck . | |
| 4,044,762 | 8/1977 | Jacobs | 128/136 |
| 4,064,628 | 12/1977 | Weitzman . | |
| 4,096,986 | 6/1978 | Florian | 229/44 R |
| 4,114,614 | 9/1978 | Kesling | 128/136 |
| 4,138,477 | 2/1979 | Gaffar | 424/52 |
| 4,138,814 | 2/1979 | Weitzman . | |
| 4,173,219 | 11/1979 | Lentine | 128/260 |
| 4,173,505 | 11/1979 | Jacobs . | |
| 4,183,914 | 1/1980 | Gaffar et al. | 424/48 |
| 4,217,342 | 8/1980 | Gaffar et al. | 424/48 |
| 4,217,343 | 8/1980 | Gaffar et al. | 424/48 |
| 4,243,658 | 1/1981 | Chang | 424/52 |
| 4,296,096 | 10/1981 | Pierce | 424/52 |
| 4,304,766 | 12/1981 | Chang | 424/52 |
| 4,348,378 | 9/1982 | Kosti | 424/7 |
| 4,366,146 | 12/1982 | Chang | 424/52 |
| 4,376,628 | 3/1983 | Aardse | 433/80 |
| 4,428,373 | 1/1984 | Seid et al. | 604/77 |
| 4,459,277 | 7/1984 | Kosti | 424/7.1 |
| 4,470,964 | 9/1984 | Chang | 424/52 |
| 4,475,888 | 10/1984 | Gores et al. | 433/42 |
| 4,485,090 | 11/1984 | Chang | 424/52 |
| 4,510,127 | 4/1985 | Chang | 424/52 |
| 4,537,765 | 8/1985 | Gaffar et al. | 424/53 |
| 4,544,354 | 10/1985 | Gores et al. | 433/42 |
| 4,590,064 | 5/1986 | Gaffar | 424/49 |
| 4,627,977 | 12/1986 | Gaffar et al. | 424/52 |
| 4,661,341 | 4/1987 | Benedict et al. | 424/48 |
| 4,672,959 | 6/1987 | May et al. | 128/136 |
| 4,791,941 | 12/1988 | Schaefer | 128/861 |
| 4,806,340 | 2/1989 | Gaffar et al. | 424/52 |
| 4,806,342 | 2/1989 | Gaffar et al. | 424/52 |
| 4,808,400 | 2/1989 | Gaffar et al. | 424/52 |
| 4,808,401 | 2/1989 | Gaffar et al. | 424/52 |
| 4,822,599 | 4/1989 | Mitra | 424/52 |
| 4,842,847 | 6/1989 | Amjad | 424/52 |
| 4,846,650 | 7/1989 | Benedict et al. | 424/55 |
| 4,847,070 | 7/1989 | Pyrz et al. | 424/52 |
| 4,869,898 | 9/1989 | Gaffar et al. | 424/52 |
| 4,871,531 | 10/1989 | Hartlaub et al. | 424/48 |
| 4,877,603 | 10/1989 | Degenhardt et al. | 424/57 |
| 4,880,619 | 11/1989 | Gaffar | 424/52 |
| 4,889,712 | 12/1989 | Gaffar et al. | 424/52 |
| 4,889,713 | 12/1989 | Gaffar et al. | 424/52 |
| 4,892,724 | 1/1990 | Amjad | 424/49 |
| 4,892,725 | 1/1990 | Amjad | 424/49 |
| 4,902,227 | 2/1990 | Smith | 433/215 |
| 4,902,497 | 2/1990 | Crisanti et al. | 424/52 |
| 4,906,456 | 3/1990 | Gaffar et al. | 424/52 |
| 4,915,937 | 4/1990 | Amjad | 424/52 |
| 4,921,692 | 5/1990 | Gaffar et al. | 424/52 |
| 4,921,693 | 5/1990 | Gaffar et al. | 424/52 |
| 4,923,684 | 5/1990 | Ibrahim et al. | 424/52 |
| 4,925,654 | 5/1990 | Gaffar et al. | 424/52 |
| 4,931,273 | 6/1990 | Gaffar et al. | 424/52 |
| 4,960,586 | 10/1990 | Suhonen | 424/52 |
| 5,009,883 | 4/1991 | Suhonen | 424/52 |

DENTAL TREATMENT TRAY FOR HOLDING MEDICAMENT GEL

RELATIONSHIP TO COPENDING APPLICATION

This application is a continuation-in-part of copending, commonly assigned application Ser. No. 07/732,480 filed Jul. 18, 1991, now abandoned, the entire contents of which are hereby incorporated by reference.

FIELD OF THE INVENTION

This invention is directed to a dental treatment tray and a combination of the tray with a medicament gel filling to be applied to the teeth and gums of a patient. More particularly, the present invention is directed to an improved dental treatment tray suitable for holding a gel containing a medicament such as a fluoride compound to be applied to the teeth and gums of a patient.

BACKGROUND OF THE INVENTION

It is often necessary for a fluoride containing gel or a gel containing another medicament to be applied to the teeth and gums of dental patients. For this purpose, it has been known to form a tray for the application of such a gel. An example of a conventional tray is that sold by Oral-B Laboratories consisting of a unitary tray structure having upper and lower cups. Each of the cups has a shape which roughly conforms to the upper or lower teeth, i.e., a generally C-shape, and has a concave medicament receiving surface. The cups are secured together by straps which normally maintain the cups in a planar relationship with both medicament receiving surfaces facing in the same direction. A gel is then loaded into the medicament receiving surfaces from a container such as a tube, after which the tray is folded about the straps so that the cups overlie one another with the medicament receiving surfaces facing away from one another. The tray, in this folded state, is then is inserted into the patient's mouth. The patient then bites down firmly into the concave medicament receiving surfaces and holds that position until the treatment is completed, after which the unit is removed from the patient's mouth and discarded.

It is important, in order to correctly position the tray in the patient's mouth, that it securely maintain its folded state as it is being inserted therein. For this purpose, the conventional Oral-B device provides a pair of handles which extend from opposite ends of the cup portions when the tray is in the unfolded state. Upon the folding of the tray, the handles overlap one another, and can be manually gripped. However, this solution has not been found to be fully satisfactory since it relies upon the ability of the technician applying the treatment to securely grip the ends of both handles without slippage. This is not always possible, and so at times the overlap and folded condition cannot be maintained and the medicament treatment is not properly carried out.

U.S. Pat. No. 4,173,219 discloses a disposable dental tray.

Treatment gels containing fluorides and other medicaments, formulated and packaged for filling and application to the teeth and gums of a patient in a dental treatment tray by a dentist are well known.

SUMMARY OF THE INVENTION

It is an object of the present invention to provide a tray for holding a medicament to be applied to the teeth and gums of a patient, which tray can be securely held in a folded state.

It is a further object of the present invention to provide a tray for holding a medicament to be applied to the teeth and gums of a patient, which tray can be easily and inexpensively manufactured.

The above and other objects are achieved according to one aspect of the present invention by an improved tray for holding the medicament to be applied to the teeth and gums of a patient, the tray being unitarily formed of a flexible material. The tray comprises a first generally C-shaped cup portion defining a first concave medicament receiving surface, a second generally C-shaped cup portion defining a second concave medicament receiving surface, and straps flexibly uniting the first and second cup portions such that the first and second cup portions normally lie substantially in a plane with ends of the first generally C-shaped cup portion facing respective ends of the second generally C-shaped cup portion, and such that the first and second concave surfaces open in the same direction. According to the invention, a handle extends from one of the cup portions in a direction away from the other of the cup portions, and a buckle extends from the other of the cup portions. The buckle comprises a tongue portion extending from the other of the cup portions and a retainer strip extending from the other of the cup portions so as to define a narrow space between the tongue portion and the retainer strip, the narrow space having a width less than the thickness of the handle. The tray may be folded over about the straps such that the cup portions overlie one another with the medicament receiving surfaces facing away from one another and such that the handle may be fitted into the narrow space. The buckle thus resiliently holds the handle so as to securely maintain the tray in the folded state.

According to another aspect of the present invention, the tray for holding medicament to be applied to the teeth and gums of a patient is unitarily formed of a flexible material and comprises first and second generally C-shaped cup portions defining respective first and second concave medicament receiving surfaces, with straps flexibly uniting the first and second cup portions such that the first and second cup portions normally lie substantially in a plane with the ends of the first generally C-shaped cup portion facing respective ends of the second generally C-shaped cup portion, and such that the first and second concave surfaces open in the same direction. First and second slotted tabs respectively extend from each of the cup portions, and in a direction away from the other of the cup portions. The slotted tabs each have a slot oriented such that the slots of the first and second slotted tabs can be interfitted to retain the train in a folded state wherein the cup portions overlie one another with the medicament receiving surfaces facing away from one another.

A still further aspect of the invention is the combination of the dental treatment tray and a treatment agent in a suitable vehicle. The vehicle can be a paste, liquid or gel and is preferably a treatment gel comprises a pharmaceutically effective amount of at least one agent for treating teeth or gums dispersed in a gel medium consisting essentially of water and an amount of a water dispersible gelling agent sufficient to form a gel. Preferably, the treatment gel comprises a agent such as from 0.05 to 5 wt. % of a soluble fluoride, either in a acidic gel or a neutral. Acidic gels can contain pharmaceutically acceptable, treatment effective amounts of phosphoric acid and hydrofluoric acid, for example. Neutral gels can have pH modifying agents such as sodium hydroxide.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
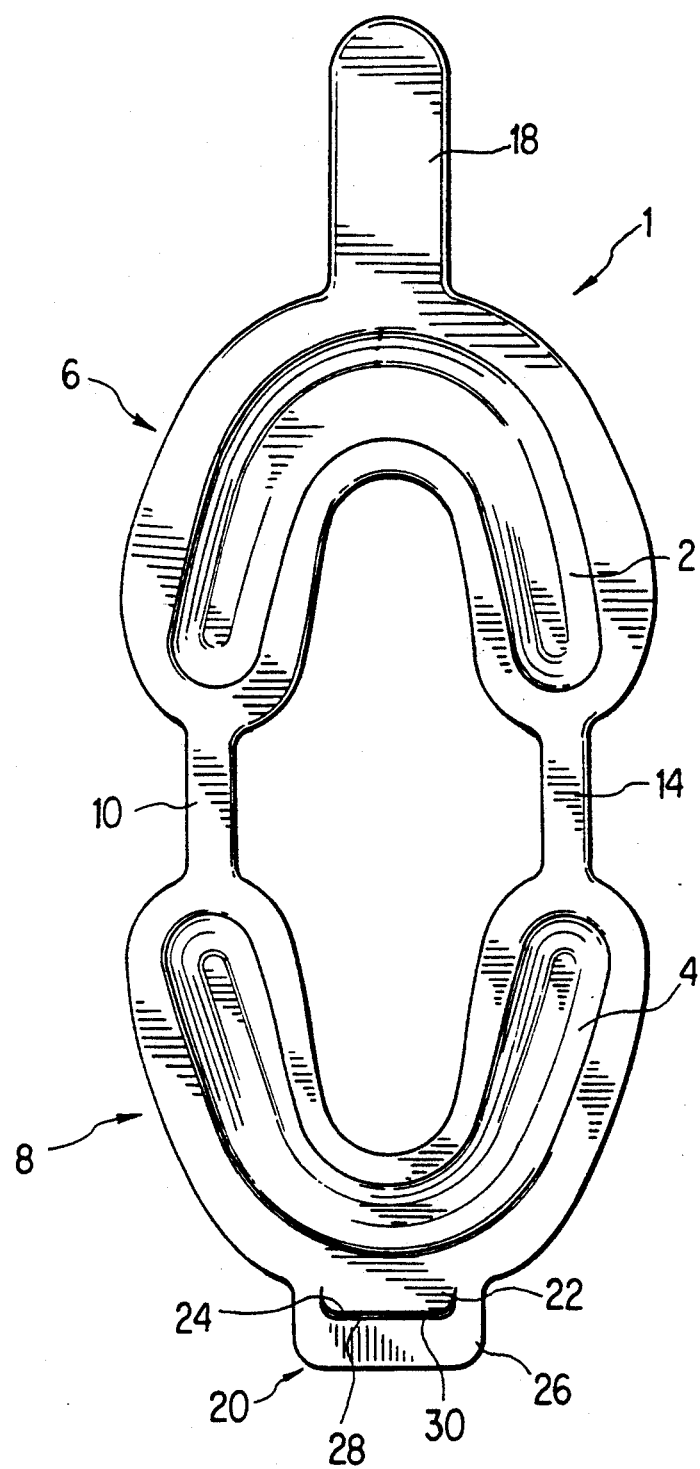
FIG. 1 is a bottom plan view of an unloaded tray according to an embodiment of the present invention in an unfolded state.

Embodiments of the present invention will now be described with reference to the attached figures, wherein the same or corresponding reference numerals will be used to identify the same or corresponding parts throughout the several views.

The tray according to the present invention is unitarily formed of foam material. Preferably, it is comprised of a relatively stiff closed cell, foam polyethylene having a layer of open cell polyurethane foam adhesively bonded thereto at the surfaces defining the concave medicament receiving surfaces.

Figure 2:
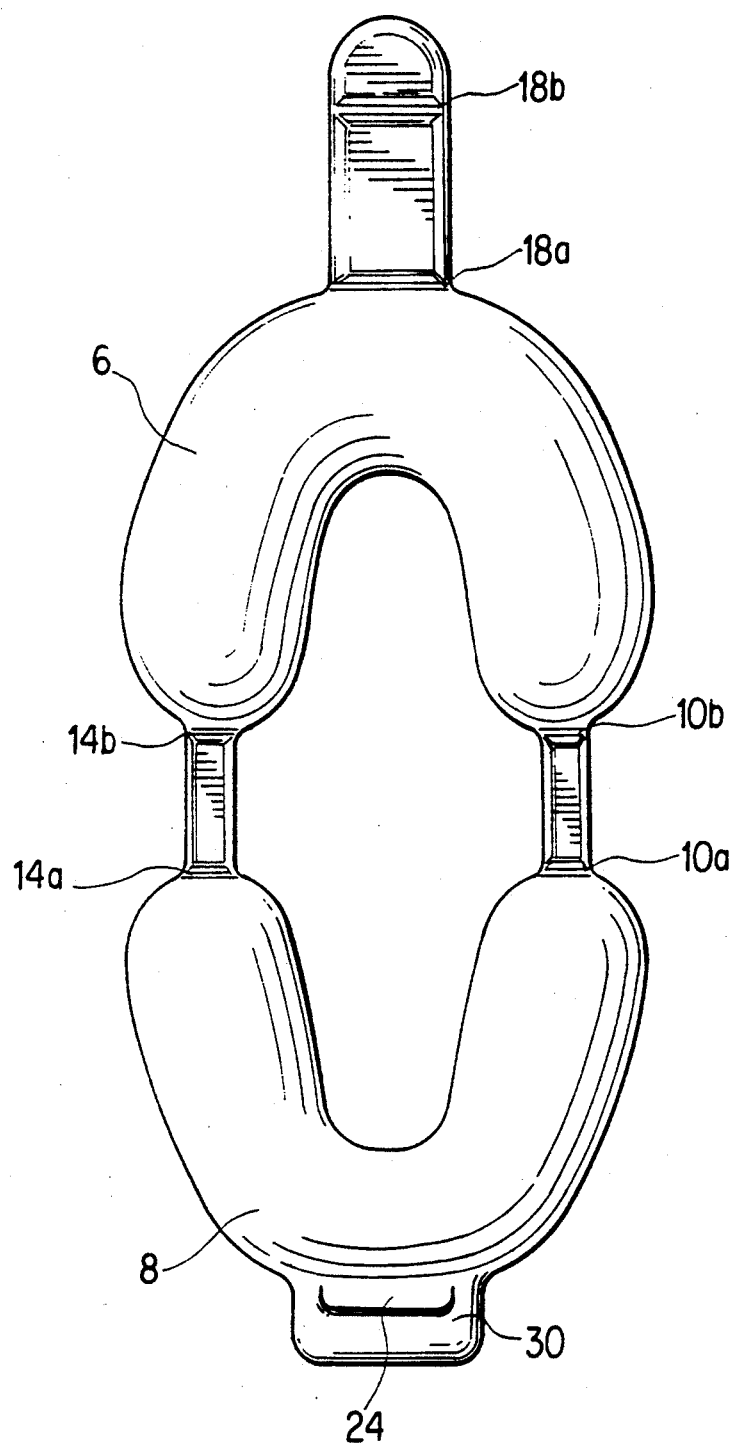
FIG. 2 is a top plan view of an unloaded tray according to the embodiment of FIG. 1 in an unfolded state.

Referring to FIGS. 1 and 2, the tray 1 according to the invention has a generally C-shaped cup portion 6 and a generally C-shaped cup portion 8, each of which is concaved to define first and second concave medicament receiving surfaces 2 and 4.

It should be noted that the cup portions 6 and 8 are generally C-shaped only insofar as this shape generally conforms to the arrangement of upper and lower teeth in a patient's jaw. Various other shapes which also generally conform to the arrangement of teeth in a patient's jaw are therefore also included within the reference to the shape of the cup portions being generally C-shaped.

The facing ends of the cup portions are flexibly united by straps 10 and 14 such that the cup portions 6 and 8 normally lie in a plane. As best seen in FIG. 2, the straps have hinge creases 10a, 10b and 14a, 14b to increase their flexibility.

The mid-portion of the cup portion 6 is provided with a unitary handle 18 which extends therefrom in a direction opposite to the cup portion 8. The handle has a hinge crease 18a at its base, and also has a tongue reception groove 18b at a position along its length, the groove 18b extending transverse to the length of the handle.

A buckle 20 extends from a mid-portion of the cup portion 8. The buckle comprises a generally rectangular tongue 22 which extends from the cup portion and forms a generally transverse edge 24. A retainer strip 26 also extends from the mid portion of the cup portion 8 so as to surround the tongue portion. The strip defines an internal edge 28 which, together with the edge 24, defines a narrow space 30, the narrow space 30 having a width less than the thickness T of the handle.

Figure 3:
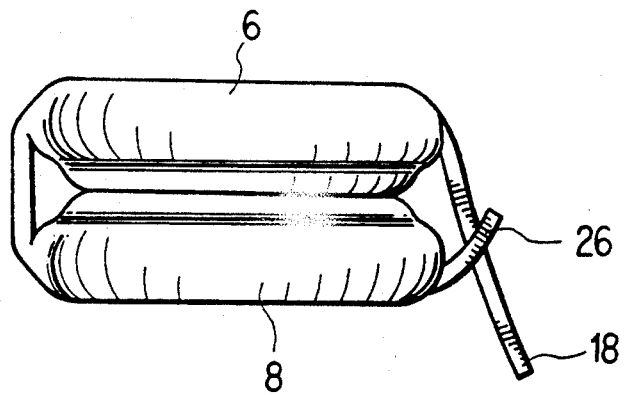
FIG. 3 is a side view of an unloaded tray according to the embodiment of FIG. 1 in a folded state.
Figure 4:
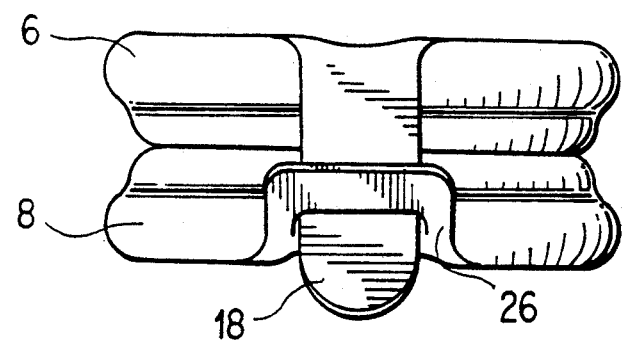
FIG. 4 is a front view of an unloaded tray according to the embodiment of FIG. 2 in a folded state.
Figure 5:
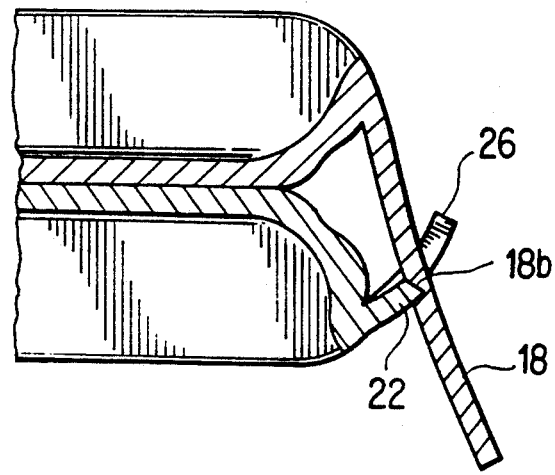
FIG. 5 is a sectional view corresponding to a portion of FIG. 4.

As seen in FIGS. 3-5, the tray can be folded over at the straps 10 and 14, so that the cup portions 6 and 8 overlie one another with the first and second concave medicament receiving surfaces facing in opposite directions. In this state, the handle 18 is inserted through the narrow space 30 until the tongue portion 22 fits into the tongue reception groove 18b. In this position, the tray is fully folded and the tongue portion 22 resiliently holds the handle, and so securely maintains the tray in the folded state. One can thus, by gripping the distal end of handle 18, insert the tray into the patient's mouth without concern for the tray accidentally shifting from the folded state. In a preferred technique, it is useful to squeeze the sides of folded gel tray together to facilitate inserting the device into a patient's mouth. Since the two sections of the gel tray are held firmly together by the latch, only one hand is needed to insert the tray.

Figure 6:
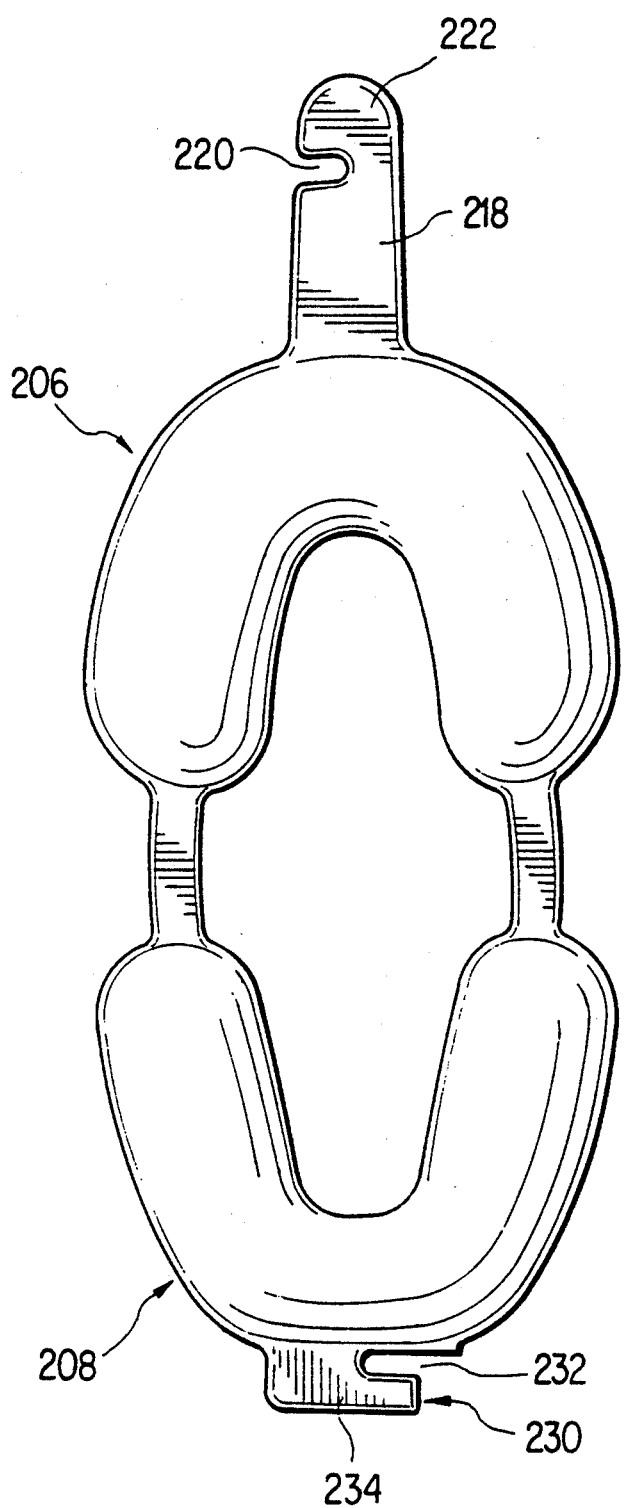
FIG. 6 is a top plan view of an unloaded tray according to another embodiment in an unfolded state.

FIG. 6 shows another embodiment which is identical to the first embodiment, except as set forth below.

In the second embodiment, a first slotted tab 218 extends from a mid-portion of the cup portion 206. The first slotted tab 218 is elongate and extends in a direction opposite the cup portion 208. A slot 220 extends from one lateral edge of the elongate slot tab 218 in a direction generally transverse to the length of the slotted tab. It terminates at a position near a longitudinal center line of the tab 218, so as to form a hook portion 222 in the region of the tab 218 which is distal of the slot 220.

A short slotted tab 230 extends from a mid portion of the cup portion 208. It includes a slot 232 extending from a lateral edge opposite the lateral edge from which the slot 220 extends, with respect to the longitudinal center line of the slot 218. The slot 232 also extends in a direction generally transverse to the length of the tab 218, so as to form a distal hook 234.

In use, when the tray is folded to the folded position shown in FIGS. 3-5, the slots are inserted into one another, so that the hook portions 222 and 234 interengage one another to securely maintain the tray in the folded position. It has been found that unlatching the tray, which is sometimes required during use, can be done more easily with this second embodiment than with the first embodiment.

The tray is designed to be loaded with a dental treatment agent in a suitable vehicle such as a gel for application to the teeth and gums of a patient. Optionally, the disposable tray can be provided to the dentist already loaded with the treatment gel to be applied. The terms "loaded" and "preloaded", as used herein, are defined to mean that some portion of the treatment agent has been placed in the trough formed by the tray's foam interior. Preferably, the amount of treatment agent loaded in the tray corresponds to the full amount which the dentist wishes to use in the dental tray treatment method.

The medicinal treatment agent contains a medicament or treatment agent for treating teeth or gums in the form of a coating, gel, paste, solution or the like. The gel, paste or solution forms of treatment agent can be applied to the brush by the dentist or it can be provided to the dentist in the preloaded form.

Medicament coatings, solutions, pastes and gels are well known and fully within the skill of the art. The preferred medicament vehicle is a gel medium. Treatment gels which are suitable for use with and for preloading the dental treatment tray of this invention are well known and fully within the skill of the art. In general, the gels comprise an aqueous solution of the medicament and pharmaceutically acceptable, non-toxic additives such as aqueous gelling agents, humectants, surfactants, coloring or whitening agents, chlorophyll compounds, flavoring agents, preservatives, optional co-solvents, stabilizers, sweeteners, dyes, and pH modifying agents. Suitable materials and manufacturing processes are described in U.S. Pat. Nos. 4,418,057, 4,254,101, 4,627,977, 4,806,340, 4,847,070, 4,902,497, 4,906,456, and 4,960,586, for example, the entire contents of each of which are incorporated by reference.

Suitable medicaments include antimicrobial treatment agents. Suitable antimicrobial agents include, but are not limited to, quaternary ammonium compounds such as cetylpyridinium chloride, domiphen bromide, benzethonium chloride and the like; antibiotics and related drugs such as nitroimidazoles (metronidazole, etc.), tetracyclines, penicillins, clindamycin, spiramycin, nystatin, amphotericin, erythromycin, and the like; essential oils such as thymol, eucalyptol, menthol, methyl salicylate, and the like; metal salts such as mercurials, zinc salts, aluminum salts, and the like; other treatment compounds such as chlorhexidine, alexidine, hexetridine, IRGASAN DP300, salicylanilides, and the like.

Suitable flavors and fragrances include organic acids, esters, and aldehydes which are both safe and pleasant. Any suitable flavoring or sweetening material may also be employed. Examples of suitable flavoring constituents are flavoring oils, e.g. oil of spearmint, peppermint, wintergreen, sassafras, clove, save, eucalyptus, marjoram, cinnamon, lemon, orange and methyl salicylate. Suitable sweetening agents include sucrose, lactose, maltose, dextrose, levulose, sorbitol, xylitol, d-tryptophan, dihydrochalcones, sodium cyclamate, perillartine, APM (aspartyl phenyl alanine, methyl ester), saccharine and the like.

Biologically active materials which can be included in the gels are growth hormones and other compounds or compositions which enhance or stimulate tissue regrowth and healing.

Oxygenating agents which can be included in the gels include sodium perborate, urea peroxide, stabilized hydrogen peroxide, and the like.

Fluorides which can be included in the gels include sodium fluoride, stabilized stannous fluoride, amine fluorides and the like. A suitable stabilized stannous fluoride treatment gel is disclosed in U.S. Pat. Nos. 4,960,586 and 5,009,883, for example, the entire contents of which are hereby incorporated by reference. The fluoride can be provided in concentrations of from 0.05 to 5.0 weight percent.

Desensitizing agents which can be included in the gels include hydroxyapatite, formaldehyde, soluble oxalates, potassium salts include potassium fluoride, and the like.

Any other soluble, non-toxic pharmaceutically acceptable material which has a beneficial or therapeutic effect on the health, integrity or appearance of oral hard and soft tissues can be incorporated in the gels.

Any conventional humectant can be used. Suitable humectants include sorbitol, glycerin, or other edible polyhydric alcohols, the natural or synthetic gums conventionally used as hardening control agents and binders.

Suitable gelling agents for use in the composition of this invention include from 0.1 to 10 and preferably from 0.5 to 5 weight percent gelling agent. Gelling agents should be colloidal silica, magnesium aluminum silicate, and silicate free compounds such as Irish moss, gum karaya, gum arabic, gum tragacanth, xanthan gum, other polysaccharide gums, starch, polyvinylpyrrolidone, hydroxyethyl propylcellulose, hydroxybutyl methyl cellulose, hydroxypropyl methyl cellulose, hydroxyethyl cellulose, sodium carboxymethyl cellulose, other hydroxyvinyl polymers, and the like.

The compositions should have a pH within the range of from 2 to 11. One embodiment of treatment gel for treating intact teeth has an acidic pH and contains hydrofluoric and phosphoric acids. A neutral treatment gel is preferred to treat teeth for which acid treatment is not suitable.

An optimum acidic gel can have the following approximate composition:

| Component | Amount, % w/w |
| --- | --- |
| Gelling agent | 2.5 |
| Glycerin | 5.0 |
| Aqueous Hydrofluoric Acid | 0.2 |
| Aqueous Phosphoric Acid | 1.5 |
| Sodium Fluoride | 2.6 |
| Sorbitol solution | 45.0 |
| Water | 41.0 |
| Xanthan Gum | 0.4 |

An optimum neutral gel can have the following composition:

| Component | Amount, % w/w |
| --- | --- |
| Gelling agent | 1.8 |
| Sodium Fluoride | 1.9 |
| Sodium Hydroxide Solution | 9.0 |
| Sorbitol Solution | 20.0 |
| Water | 65.2 |

This invention is further illustrated by the following specific but non-limiting examples of suitable gels which can be applied to the dental treatment tray of this invention.

EXAMPLE 1

Acidic Minute Treatment Gel

The following ingredients are combined to produce an acidic Minute Treatment Gel used for fluoride treatment of teeth.

| Component | Amount, % w/w |
| --- | --- |
| Carbopol[a] | 2.500 |
| FD & C Yellow #10 (1.0% aq. solution) | 0.085 |
| FD & C Blue #1 (1.0% aq. solution) | 0.025 |
| Glycerin 96% USP | 5.000 |
| Hydrofluoric Acid, 48% AR | 0.174 |
| Phosphoric Acid 75%, Food Grade | 1.490 |
| Prosweet Liquid[b] | 1.000 |
| Sodium Fluoride, USP | 2.599 |
| Sodium Saccharin USP Crystals | 0.210 |
| Sorbitol 70.0% Solution USP | 45.000 |
| Spearmint Oil NF, Extra | 0.600 |
| Titanium Dioxide USP | 0.010 |

-continued

| Component | Amount, % w/w |
| --- | --- |
| Water, Purified USP | 40.927 |
| Xanthan Gum[c] | 0.380 |

[a]CARBOMER 934P NF, carboxyvinyl polymer
[b]F & C International
[c]KELTROL, Kelco

EXAMPLE 2

Neutral Treatment Gel

The following ingredients are combined to produce an Neutral Treatment Gel used for fluoride treatment of teeth.

| Component | Amount, % w/w |
| --- | --- |
| Carbopol 934P[a] | 1.800 |
| FD & C Blue #1 (1.0% Solution) | 0.054 |
| FD & C Red #33 (1.0% Solution) | 0.123 |
| Grape Flavor #11540[b] | 0.500 |
| Methylparaben NF | 0.150 |
| Propylparaben NF | 0.050 |
| Prosweet Liquid[c] | 1.000 |
| Sodium Fluoride, USP | 1.870 |
| Sodium Hydroxide (10% Solution) | 9.000 |
| Sodium Saccharin USP Crystals | 0.210 |
| Sorbitol Solution 70% USP | 20.000 |
| Titanium Dioxide USP | 0.010 |
| Water, Purified USP | 65.233 |

[a]CARBOMER 934P NF, carboxyvinyl polymer
[b]Bush, Boake & Allen
[c]F & C International Obviously, numerous modifications and variations of the present invention are possible in light of the above teachings. It is therefore to be understood that within the scope of the appended claims, the invention may be practiced otherwise than as specifically described herein.

The invention claimed is:

1. A tray for holding medicament to be applied to the teeth and gums of a patient, said tray being unitarily formed of a flexible material and comprising:
   a first generally C-shaped cup portion defining a first concave medicament receiving surface;
   a second generally C-shaped cup portion defining a second concave medicament receiving surface;
   straps flexibly uniting said first and second cup portions such that said first and second cup portions normally lie substantially in a plane with ends of said first generally C-shaped cup portion facing respective ends of said second generally C-shaped cup portion, and such that said first and second concave surfaces open in the same direction;
   a handle extending from one of said cup portions in a direction away from the other of said cup portions; and
   a buckle extending from said other of said cup portions, said buckle comprising a tongue portion extending from said other of said cup portions and a retainer strip extending from said other of said cup portions so as to define a narrow space between tongue portion and said retainer strip, said narrow space having a width less than the thickness of said handle,
   whereby said tray may be folded about said straps such that said cup portions overlie one another with said medicament receiving surfaces facing away from one another and such that said handle may be fitted into said narrow space, and whereby the buckle resiliently holds said handle so as to securely maintain said tray in the folded state.

2. A tray of claim 1, wherein said medicament receiving surfaces are formed of an open cell foamed material.

3. A tray of claim 2, wherein surfaces of said tray, other than said medicament receiving surfaces, is formed of a closed cell, foam polyethylene, and said medicament receiving surfaces are formed of an open cell polyurethane foam.

4. A tray of claim 3, wherein said open cell polyurethane foam is adhesively bonded to said closed cell, foam polyethylene.

5. A tray of claim 1, including a reduced thickness groove formed in said handle at a position along the length of said handle such that said groove is held in said narrow space when said tray is in said folded state.

6. A tray of claim 5, wherein said tray is formed of a sufficiently stiff material to maintain said tray substantially rigid when in said folded state with groove held in said narrow space.

7. A tray of claim 5, wherein said handle has a length sufficient that a distal end thereof can be manually held when said tray is in said folded state.

8. A tray of claim 1, wherein said straps connect said facing ends of said first and second cup portions.

9. A tray of claim 1 in combination with a treatment agent comprising a pharmaceutical effective amount of at least one agent for treating gums or teeth in a non-toxic, pharmaceutically acceptable vehicle.

10. A tray of claim 9 in combination with a treatment gel comprising a pharmaceutically effective amount of at least one agent for treating teeth or gums dispersed in a gel medium consisting essentially of water and an amount of a water dispersible gelling agent sufficient to form a gel.

11. A tray of claim 10 wherein the treatment gel contains from 0.05 to 5 wt. % of a soluble fluoride.

12. A tray of claim 11 wherein the treatment gel has an acidic pH and contains pharmaceutically acceptable, treatment effective amounts of phosphoric acid and hydrofluoric acid.

13. A tray of claim 12 wherein the treatment gel consists essentially of the following approximate composition:

| Component | Amount, % w/w |
| --- | --- |
| Gelling agent | 2.5 |
| Glycerin | 5.0 |
| Aqueous Hydrofluoric Acid | 0.2 |
| Aqueous Phosphoric Acid | 1.5 |
| Sodium Fluoride | 2.6 |
| Sorbitol solution | 45.0 |
| Water | 41.0 |
| Xanthan Gum | 0.4 |

14. A tray of claim 11 wherein the treatment gel has a substantially neutral pH.

15. A tray of claim 14 wherein the treatment gel consists essentially of the following approximate composition:

| Component | Amount, % w/w |
| --- | --- |
| Gelling agent | 1.8 |
| Sodium Fluoride | 1.9 |
| Sodium Hydroxide Solution | 9.0 |
| Sorbitol Solution | 20.0 |

-continued

| Component | Amount, % w/w |
|---|---|
| Water | 65.2 |

16. A gel tray for holding a gel medicament to be applied to the teeth and gums of a patient, said tray being unitarily formed of a laminate of relatively stiff closed cell polyethylene and absorbent open cell polyurethane, said tray comprising:
a first generally C-shaped cup portion defining a first concave medicament receiving surface;
a second generally C-shaped cup portion defining a second concave medicament receiving surface;
straps flexibly uniting said first and second cup portions such that said first and second cup portions normally lie substantially in a plane with ends of said first generally C-shaped cup portion facing respective ends of said second generally C-shaped cup portion, and such that said first and second concave surfaces are open in the same direction;
an elongate handle extending from one of said cup portions in a direction away from the other of said cup portions, said elongate handle having a tongue reception groove extending transverse to the length of the handle;
a buckle extending from the other of said cup portions, said buckle comprising a rectangular tongue portion extending from said other of said cup portions and a retainer strip extending from said other of said cup portions so as to surround said tongue portion and to define a narrow space between the tongue portion and said retainer strip, said narrow space having a width less than the thickness of the handle but sufficient to accommodate said tongue reception groove,
whereby said tray may be folded about said straps such that said cup portions overlie one another with said medicament receiving surfaces facing away from one another and such that said handle may be fitted into said narrow space with said tongue engaged in said tongue reception groove, and
whereby the buckle resiliently holds said handle so as to securely maintain said tray in the folded state.

17. A tray of claim 16, wherein said open cell polyurethane foam is adhesively bonded to said closed cell, foam polyethylene.

18. A tray for holding medicament to be applied to the teeth and gums of a patient, said tray being unitarily formed of a flexible material and comprising:
a first generally C-shaped cup portion defining a first concave medicament receiving surface;
a second generally C-shaped cup portion defining a second concave medicament receiving surface;
straps flexibly uniting said first and second cup portions such that said first and second cup portions normally lie substantially in a plane with ends of said first generally C-shaped cup portion facing respective ends of said second generally C-shaped cup portion, and such that said first and second concave surfaces open in the same direction;
a first slotted tab extending from one of said cup portions in a direction away from the other of said cup portions; and
a second slotted tab extending from said other of said cup portions in a direction away from said one of said cup portions,
wherein said first and second slotted tabs each has a slot oriented such that said slots of said first and second slotted tabs may be interfitted to retain said tray in a folded state wherein said cup portions overlie one another with said medicament receiving surfaces facing away from one another.

19. A tray of claim 18, wherein said first slotted tab is elongate.

20. A tray of claim 19, wherein said slots define hooks at distal ends of said first and second tabs, said hooks interengaging one another when said slots are interfitted.

21. A tray of claim 20, wherein said slots extend from side edges of their respective tabs, which side edges are respectively on opposite sides of a longitudinal center line of said elongate slotted tab.

22. A tray of claim 18, wherein said medicament receiving surfaces are formed of an open cell foamed material.

23. A tray of claim 22, wherein surfaces of said tray, other than said medicament receiving surfaces, are formed of a closed cell, foam polyethylene and said medicament receiving surfaces are formed of an open cell polyurethane foam.

24. A tray of claim 18, wherein said tray is formed of a sufficiently stiff material to maintain said tray substantially rigid when in said folded state.

25. A tray of claim 18, wherein said straps connect said facing ends of said first and second cup portions.

26. A tray of claim 18 in combination with a treatment gel comprising a pharmaceutically effective amount of at least one agent for treating teeth or gums dispersed in a gel medium consisting essentially of water and an amount of a water dispersible gelling agent sufficient to form a gel.

27. A tray of claim 26 wherein the treatment gel contains from 0.05 to 5 wt. % of a soluble fluoride.

28. A tray of claim 27 wherein the treatment gel has an acidic pH and contains pharmaceutically acceptable, treatment effective amounts of phosphoric acid and hydrofluoric acid.

29. A tray of claim 28 wherein the treatment gel consists essentially of the following approximate composition:

| Component | Amount, % w/w |
|---|---|
| Gelling agent | 2.5 |
| Glycerin | 5.0 |
| Aqueous Hydrofluoric Acid | 0.2 |
| Aqueous Phosphoric Acid | 1.5 |
| Sodium Fluoride | 2.6 |
| Sorbitol solution | 45.0 |
| Water | 41.0 |
| Xanthan Gum | 0.4 |

30. A tray of claim 27 wherein the treatment gel has a substantially neutral pH.

31. A tray of claim 30 wherein the treatment gel consists essentially of the following approximate composition:

| Component | Amount, % w/w |
|---|---|
| Gelling agent | 1.8 |
| Sodium Fluoride | 1.9 |
| Sodium Hydroxide Solution | 9.0 |
| Sorbitol Solution | 20.0 |
| Water | 65.2 |

* * * * *